United States Patent
Bingham et al.

(10) Patent No.: US 11,141,360 B2
(45) Date of Patent: *Oct. 12, 2021

(54) PERSONAL CARE COMPOSITION WITH INCREASED VAPOR RELEASE

(71) Applicant: The Procter & Gamble Company, Cincinnati, OH (US)

(72) Inventors: Stephen Bingham, Basingstoke (GB); Barbara Jackova, Issy les Moulineaux (FR); Joshua Hampton, Frankfurt (DE); Jason William Newlon, Lebanon, OH (US); Jaspreet Singh Kochhar, Singapore (SG); Jayant Khanolkar, Singapore (SG); Aline Fornear, Twickenham (GB)

(*) Notice: Subject to any disclaimer, the term of this patent is extended or adjusted under 35 U.S.C. 154(b) by 0 days.

This patent is subject to a terminal disclaimer.

(21) Appl. No.: 16/717,151

(22) Filed: Dec. 17, 2019

(65) Prior Publication Data

US 2020/0188241 A1     Jun. 18, 2020

Related U.S. Application Data

(60) Provisional application No. 62/780,964, filed on Dec. 18, 2018.

(51) Int. Cl.
  *A61K 8/04*   (2006.01)
  *A61K 8/34*   (2006.01)
  *A61K 8/92*   (2006.01)

(52) U.S. Cl.
  CPC ............... *A61K 8/042* (2013.01); *A61K 8/34* (2013.01); *A61K 8/922* (2013.01); *A61K 2800/412* (2013.01); *A61K 2800/48* (2013.01)

(58) Field of Classification Search
  None
  See application file for complete search history.

(56) References Cited

U.S. PATENT DOCUMENTS

| | | | |
|---|---|---|---|
| 5,175,152 A | 12/1992 | Singh | |
| 5,621,012 A | 4/1997 | Schoenrock | |
| 7,347,989 B2 | 3/2008 | Walling | |
| 8,679,469 B2 | 3/2014 | Allison | |
| 2008/0015295 A1 | 1/2008 | Williams | |
| 2008/0193387 A1 | 8/2008 | De | |
| 2009/0181071 A1* | 7/2009 | St. John | A61K 8/0208 424/443 |
| 2009/0280076 A1 | 11/2009 | Yoshida | |
| 2009/0280077 A1 | 11/2009 | Yoshida | |
| 2012/0219520 A1 | 8/2012 | Allison | |
| 2012/0225026 A1 | 9/2012 | Hurry | |
| 2013/0004441 A1 | 1/2013 | Bui | |
| 2014/0274982 A1 | 9/2014 | Bakan | |

FOREIGN PATENT DOCUMENTS

| | | |
|---|---|---|
| CA | 2173153 A1 | 2/1996 |
| CN | 108451781 A | 8/2018 |
| FR | 2743566 A1 | 7/1997 |
| FR | 2820739 A1 | 8/2002 |
| GB | 9925006 | 12/1999 |
| WO | WO02094900 A1 | 11/2002 |
| WO | WO2003102104 A1 | 12/2003 |
| WO | WO2004014438 A1 | 2/2004 |
| WO | WO2004105707 A1 | 7/2006 |
| WO | WO2011030265 A1 | 3/2011 |
| WO | WO2018037121 A1 | 3/2018 |

OTHER PUBLICATIONS

U.S. Appl. No. 16/717,135, filed Dec. 17, 2019, Bingham et al.
PCT Search Report and Written Opinion for PCT/US2019/066781 dated Apr. 6, 2020.
Anonymous—Vapour Rub, database gnpd Mintel Jan. 4, 2008—retrieved from www.gnpd.com accession No. 836700.
Anonymous, "Vapor Stick", online database GNPD Mintel; Oct. 21, 2016, retrieved from www.gnpd.com—accession No. 4368391.

* cited by examiner

*Primary Examiner* — Bethany P Barham
*Assistant Examiner* — Barbara S Frazier
(74) *Attorney, Agent, or Firm* — Jason Jeffrey Camp; Amanda Herman Berghauer

(57) ABSTRACT

Provided herein is a personal care composition that can exhibit an increased vapor release while maintaining physical stability and texture. The personal care composition can have from about 35% to about 90% petrolatum, an additional microcrystalline wax having a needle penetration at 25° C. of from about 35 to about 75 dmm, from about 1% to about 8% of a gelling agent mixture, and from about 20% to about 50% of an olfactory composition, all by weight of the composition.

16 Claims, No Drawings

PERSONAL CARE COMPOSITION WITH INCREASED VAPOR RELEASE

FIELD OF THE INVENTION

Described herein is a personal care composition, and more particularly a petrolatum-based personal care composition comprising an olfactory composition and an additional microcrystalline wax, wherein the personal care composition exhibits increased vapor release while maintaining physical stability and a consumer acceptable texture.

BACKGROUND OF THE INVENTION

Personal care compositions are routinely used by consumers on the chest, back and/or throat to provide relief from nasal congestion, dry cough, chest congestion, muscle aches and/or pains, and difficulty sleeping due to the common cold and/or flu. Olfactory compositions can be released from the personal care composition as vapors, which are inhaled through the nose and can provide the sensation of cooling and relief. However, some consumers find that current products are not strong enough to provide the desired level of symptom relief. It has been found that a product that provides a stronger sensory experience and smell can be perceived by the consumer as a stronger, more effective product.

One way to formulate a product with an increased perception of strength is to increase the level of olfactory composition in the formula. However, it is difficult to formulate a personal care composition with an increased olfactory composition content. As the olfactory composition concentration increases, physical stability decreases, which can affect both the appearance of the final product as well as the distribution of the olfactory composition within the composition. Without being limited by theory, it is believed that petrolatum forms an internal scaffold into which drops of the olfactory composition are dispersed. Once the maximum carrying capacity of the petrolatum is exceeded, droplets can form on the surface of the product. This process is commonly referred to as "bleeding" or "sweating" and may be unacceptable to consumers. Increasing olfactory composition level can also increase the greasiness of a personal care composition, which can affect the skin feel of the product and may leave an oil residue on clothing and other fabrics. Finally, at high levels, olfactory compositions may be irritating to the skin, causing pain and/or skin reddening.

As such, there is a need for a personal care composition that provides a strong sensory experience that is noticeable to users without irritating the skin and while maintaining physical stability and texture.

SUMMARY OF THE INVENTION

Described herein is a personal care composition comprising: (a) from about 35% to about 90% petrolatum, by weight of the composition; (b) an additional microcrystalline wax having a needle penetration at 25° C. of from about 35 to about 75 dmm; (c) from about 1% to about 6% of a gelling agent mixture, by weight of the composition; and (d) from about 20% to about 50% of an olfactory composition, by weight of the composition.

Described herein is a personal care composition comprising: (a) greater than about 35% petrolatum, by weight of the composition; (b) from about 2.5% to about 20%, by weight of the composition, of an additional microcrystalline wax wherein the microcrystalline wax has a needle penetration at 25° C. of from about 35 to about 75 dmm; and (c) from about 20% to about 50% of an olfactory composition, by weight of the composition.

Described herein is a personal care composition comprising: (a) from about 35 to about 90% petrolatum, by weight of the composition; (b) an additional microcrystalline wax having a needle penetration at 25° C. of from about 35 to about 75 dmm; and (c) an olfactory composition; wherein the personal care composition has vapor release of greater than about 35 mg at 8 hours as measured by the Vapor Release Test Method.

Described herein is a personal care composition comprising: (a) greater than about 35% petrolatum, by weight of the composition; (b) from about 2.5% to about 20%, by weight of the composition, of an additional microcrystalline wax; and (c) from about 20% to about 50% of an olfactory composition, by weight of the composition; wherein the personal care composition has vapor release of greater than about 50 mg at 8 hours as measured by the Vapor Release Test Method.

DETAILED DESCRIPTION OF THE INVENTION

As used herein, the articles "a" and "an" are understood to mean one or more of the material that is claimed or described, for example, "a gelling agent".

As used herein, "olfactory composition" refers to a composition comprising odoriferous material(s) which are able to provide a fragrance. The odoriferous materials can be olfactory agents and can include aromatic oils, excipients, actives and/or perfumes.

As used herein, "microcrystalline wax" means a refined mixture of solid, saturated aliphatic hydrocarbons and is produced by de-oiling certain fractions from the petroleum refining process.

Microcrystalline waxes differ from refined paraffin wax in that the molecular structure is more branched and the hydrocarbon chains are longer (higher molecular weight). As a result, the crystal structure of microcrystalline wax is much finer than paraffin wax, and this can directly impact many of the physical properties. Microcrystalline waxes are tougher, more flexible and generally higher in melting point than paraffin wax at the same molecular weight. As described herein, there are three categories of microcrystalline waxes based on its needle penetration at 25° C. (a measure of hardness as determined under ASTM test method D 1321, July 2016). A first category of microcrystalline wax exhibits a needle penetration at 25° C. of about 35 to about 75 dmm (decimillimeter). A second category of microcrystalline wax exhibits a needle penetration at 25° C. of about 20 to about 34 dmm. A third category of microcrystalline wax exhibits a needle penetration at 25° C. of about 14 to about 19 dmm.

All weights, measurements and concentrations herein are measured at 23 degrees Celsius (° C.) and 50% relative humidity, unless otherwise specified.

All percentages, parts and ratios as used herein are by weight of the total personal care composition, unless otherwise specified. All such weights as they pertain to listed ingredients are based on the active level and, therefore do not include solvents or by-products that may be included in commercially available materials, unless otherwise specified.

The composition and methods of the present invention can comprise, consist of, or consist essentially of, the essential elements and limitations of the invention described herein, as well as any additional or optional ingredients, components, or limitations described herein or otherwise useful in personal health care compositions intended for use by a subject.

Consumers are looking for personal care compositions that can provide a stronger sensory experience and smell. However, it is challenging to incorporate a higher level of an olfactory composition in petrolatum based personal care compositions because it can decrease physical stability and leave the product feeling greasy, which can be unacceptable to consumers. It was surprisingly found that the inclusion of certain types of additional waxes, preferably microcrystalline waxes having a needle penetration at 25° C. of from about 20 to about 75 dmm, in a personal care composition comprising an increased olfactory composition level can improve the firmness and physical stability without significantly disrupting vapor release. Microcrystalline waxes having a needle penetration at 25° C. of less than about 20 dmm in similar personal care compositions significantly disrupted vapor release after 8 hours and/or increased the firmness of the composition to a point which may be unacceptable to consumers for topical applications. It was further found that the combination of additional microcrystalline wax and a gelling agent mixture can provide a synergistic effect on the physical stability of the personal care composition. As described herein, vapor release can be determined by measuring mass loss over time.

Described herein is a personal care composition comprising greater than about 35% of a petrolatum, from about 20 to about 50% of an olfactory composition, by weight of the composition, and an additional microcrystalline wax, wherein the microcrystalline wax has a needle penetration at 25° C. of about 35 to about 75 dmm. Also described herein is a personal care composition comprising greater than about 35% of a petrolatum, from about 20 to about 50% of an olfactory composition, by weight of the composition, and an additional microcrystalline wax, wherein the microcrystalline wax has a needle penetration at 25° C. of about 20 to about 34 dmm.

Petrolatum

The personal care composition can comprise petrolatum. The petrolatum useful in the composition described herein can be any grade of white or yellow petrolatum recognized in the art as suitable for human application. Examples of suitable petrolatum can include: Snow White Pet—C from Calumet Specialty Products, Indianapolis, Ind. (melting range: 51-54° C.), Snow White V30 from Sonneborn, Parsippany, N.J. (melting range: 55-64° C.), Rajell WP1008AB5 Silkolene/Raj from Raj Petro Specialties P. Ltd., Mumbai, India (melting range: 65-68° C.), Rajell WP 29 AJB from Raj Petro Specialties P. Ltd., (melting range: 63-69° C.), Pet Blend 670 PG from Calumet Specialty Products, (melting range: 64-72° C.), Merkur 873 from Sasol Performance Chemicals, Hamburg, Germany (melting range: 55-64° C.), equivalents thereof, and mixtures thereof.

In one aspect, the petrolatum can have a melting range of from about 35° C. to about 75° C., alternatively from about 40° C. to about 70° C., alternatively from 45° C. to about 65° C., alternatively from about 55° C. to about 65° C. In one aspect, the petrolatum can have a melting range of from about 38° C. to about 60° C. The melting range of petrolatum can be measured according to ASTM test method D127, February 2015.

In one aspect, the personal care composition can comprise from about 35% to about 90% petrolatum, alternatively from about 50% to about 85%, alternatively from about 60% to about 75%, alternatively from about 65% to about 70%, all by weight of the composition. In one aspect, the personal care composition can comprise from about 50% to about 90% petrolatum, by weight of the composition. In one aspect, the personal care composition can comprise greater than about 50% petrolatum, alternatively greater than about 55%, alternatively greater than about 60%, all by weight of the composition.

Gelling Agent Mixture

The personal care composition can comprise a gelling agent mixture comprising a gelling agent and a solvent.

The gelling agent can be dissolved in a solvent to form a gelling agent mixture. Without being limited by theory, it is believed that the gelling agent mixture can self-assemble to form a solid gel than can lock in droplets of the olfactory composition in a network and thereby can prevent the olfactory composition from separating from the product. One advantage to trapping the olfactory composition in a network is that the oil concentration can be increased without the oil separating from the petrolatum base, resulting in a physically stable product. At the same time, it is believed that this network can provide an open structure that that can allow easier diffusion of the olfactory composition, making it more susceptible to coming out of the structure and giving an exponentially larger vapor release as compared to compositions without a gelling agent mixture.

In one aspect, the personal care composition can comprise from about 0.5% to about 10% of a gelling agent mixture, alternatively from about 0.75% to about 8%, alternatively from about 1% to about 6%, alternatively from about 2.5% to about 5%, all by weight of the composition. Preferably, the personal care composition can comprise about 2.5% gelling agent mixture, by weight of the composition.

Gelling Agent:

Non-limiting examples of gelling agents can include dibutyl lauroyl glutamide, dibutyl ethylhexanoyl glutamide, N-acyl amino acid derivatives such as N-acyl amino acid amides and N-acyl amino acid esters prepared from glutamic acid, lysine, glutamine, aspartic acid and combinations thereof. Non-limiting examples of N-acyl amino acid derivatives can include N-lauroyl-glutamic acid diethyl amide, N-lauroyl-glutamic acid dihexyl amide, N-lauroyl-glutamic acid dioctyl amide, N-lauroyl-glutamic acid didecyl amide, N-lauroyl-glutamic acid didodecyl amide, N-lauroyl-glutamic acid ditetradecyl amide, N-lauroyl-glutamic acid dihexadecyl amide, N-lauroyl-glutamic acid distearyl amide, N-stearoyl-glutamic acid dibutyl amide, N-stearoyl-glutamic acid dihexyl amide, N-stearoyl-glutamic acid diheptyl amide, N-stearoyl-glutamic acid dioctyl amide, N-stearoyl-glutamic acid didecyl amide, N-stearoyl-glutamic acid didodecyl amide, N-stearoyl-glutamic acid ditetradecyl amide, N-stearoyl-glutamic acid dihexadecyl amide, N-stearoyl-glutamic acid distearyl amide, and combinations thereof. Preferably, the gelling agent comprises dibutyl lauroyl glutamide and dibutyl ethylhexanoyl glutamide.

One advantage to using a gelling agent comprising both dibutyl lauroyl glutamide and dibutyl ethylhexanoyl glutamide in a personal care composition is that the combination can provide increased vapor release and physical stability as compared to a composition with either dibutyl lauroyl glutamide or dibutyl ethylhexanoyl glutamide alone. Without being limited by theory, it is believed that either dibutyl lauroyl glutamide or dibutyl ethylhexanoyl glutamide alone builds an inferior fiber network within the petrolatum in which to trap the olfactory composition droplets and may not allow as much diffusion of the olfactory composition to the surface of the composition as compared to compositions comprising both dibutyl lauroyl glutamide and dibutyl ethylhexanoyl glutamide.

The gelling agent mixture can comprise from about 0.15 to about 1% of a gelling agent, by weight of the composition, alternatively from about 0.20 to about 0.95%, alternatively from about 0.40 to about 0.85%, alternatively from about 0.50 to about 0.75%. In one aspect, the gelling agent mixture can comprise from about 0.20% to about 0.50% of a gelling agent, by weight of the composition.

The gelling agent can comprise from about 0.01% to about 1% dibutyl lauroyl glutamide, by weight of the composition, alternatively from about 0.05% to about 0.85%, alternatively from about 0.10% to about 0.60%, alternatively from about 0.20% to about 0.40%. The personal care composition can comprise from about 0.01% to about 0.40% dibutyl lauroyl glutamide, by weight of the composition.

The gelling agent can comprise from about 0.01% to about 1% dibutyl ethylhexanoyl glutamide, by weight of the composition, alternatively from about 0.05% to about 0.85%, alternatively from about 0.10% to about 0.60%, alternatively from about 0.20% to about 0.40%. The personal care composition can comprise from about 0.01% to about 0.40% dibutyl ethylhexanoyl glutamide, by weight of the composition.

In one aspect, the gelling agent can comprise about 0.20% dibutyl ethylhexanoyl glutamide and about 0.30% dibutyl lauroyl glutamide, by weight of the composition. Alternatively, the personal care composition can comprise about 0.30% dibutyl ethylhexanoyl glutamide and about 0.20% dibutyl lauroyl glutamide, all by weight of the composition.

Without being limited by theory it is believed that including a gelling agent within this range can increase the vapor release and physical stability of a personal care comprising petrolatum as compared to control compositions without a gelling agent. It was found that as the level of gelling agent increases, the vapor release increases to a maximum evaporative loss and that the inclusion of additional gelling agent beyond this threshold may only impact the firmness and physical stability, with little to no impact on vapor release. Without being limited by theory, it is believed that if the personal care composition is too firm, the texture may be unacceptable to consumers.

The ratio of dibutyl lauroyl glutamide to dibutyl ethylhexanoyl glutamide can be from about 1:4 to about 4:1, alternatively from about 1:1.5 to about 1.5:1. Preferably, the ratio of dibutyl lauroyl glutamide to dibutyl ethylhexanoyl glutamide is about 1:1.5.

Solvent:

The gelling agent mixture can comprise a solvent. Preferably, the solvent is polar and protic. One advantage to using a polar, protic solvent is that it can dissolve the gelling agent and can adjust the melting point and dissolution temperature of the gelling agent mixture. Without the presence of a solvent or if the solvent level is too low, molten petrolatum may prematurely gel and leave behind a solid gel in the processing equipment, resulting in a loss of material. Premature gelling can also make processing challenging because it can make the petrolatum difficult to pour and can clog equipment nozzles.

Solvents useful in the compositions described herein can be any solvent capable of lowering the melting point of the petrolatum/gelling agent mixture, preferably by at least 15° C., and is recognized in the art as suitable for human application. Non-limiting examples of solvents can include glycols such as pentylene glycol, propylene glycol, and hexylene glycol; diols such as 3-methyl-1,3-butanediol, 3-methyl-1,2-butanediol, and 1,5-pentanediol; glycerol, glycerol esters, and combinations thereof.

The gelling agent mixture can comprise a solvent selected from the group consisting of pentylene glycol, propylene glycol, hexylene glycol, 3-methyl-1,3-butanediol, 3-methyl-1,2-butanediol, 1,5-pentanediol, and combinations thereof. Preferably the solvent is 3-methyl-1,3-dibutanediol.

The gelling agent mixture can comprise a solvent comprising the following structure

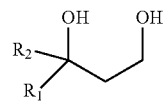

wherein R1 and R2 can be independently selected from a C1-C4 alkyl group such as methyl, ethyl, propyl or butyl.

In one aspect, the solvent does not comprise octyl dodecanol, Isostearyl alcohol, Myristyl alcohol, Cetyl alcohol, Cetearyl alcohol, Oleyl alcohol, Stearyl alcohol, isostearyl isostearate, isopropyl myristate, or combinations thereof. Without being limited by theory, it is believed that octyl dodecanol, Isostearyl alcohol, Myristyl alcohol, Cetyl alcohol, Cetearyl alcohol, Oleyl alcohol, Stearyl alcohol may not sufficiently adjust the melting point and dissolution temperature of the gelling agent mixture. In addition, it is believed that isostearyl isostearate and/or isopropyl myristate will raise the melting point of the gelling agent mixture to an unacceptable level.

The personal care composition can comprise from less than about 10% of a solvent, alternatively less than about 8%, alternatively less than about 5%, alternatively less than about 3%, all by weight of the composition. The personal care composition can comprise from about 0.5% to about 10% of a solvent, alternatively from about 0.75% to about 8%, alternatively from about 1% to about 5%, all by weight of the composition.

The gelling agent mixture can comprise a weight ratio of gelling agent to solvent of from about 1:2 to about 1:10, alternatively from about 1:3 to about 1:5. Preferably, the weight ratio of gelling agent to solvent is about 1:5.

The gelling agent mixture can comprise a weight ratio of dibutyl lauroyl glutamide:dibutyl ethylhexanoyl glutamide: solvent of about 1.2:0.8:10, alternatively from about 1:1.5:10.

Additional Wax

The personal care composition can comprise an additional wax selected from the group consisting of microcrystalline wax, paraffin wax, beeswax, and combinations thereof. In one aspect, the additional wax can comprise microcrystalline wax and paraffin wax. Preferably, the additional wax is a microcrystalline wax.

The additional wax can exhibit a drop melting point of from about 60° C. to about 77° C., alternatively from about 64° C. to about 70° C. In one aspect, the additional wax can have a drop melting point of from about 68° C. to about 77° C., alternatively from about 65° C. to about 69° C. Drop melting point can be measured according to the US Pharmacopeia <741> Melting Range Test Method (Class III).

The needle penetration at 25° C. of the additional wax can be from about 35 to about 75 dmm, alternatively from about 40 to about 60 dmm, alternatively from about 35 to about 45 dmm. In one aspect, the needle penetration at 25° C. of the additional wax is greater than about 20 dmm, alternatively greater than about 35 dmm, alternatively greater than about 40 dmm, alternatively greater than about 55 dmm. The needle penetration at 25° C. of the microcrystalline wax can be about 40 dmm, preferably about 60 dmm. Alternatively, the needle penetration at 25° C. of the microcrystalline wax can be from about 20 to about 34 dmm, alternatively from about 22 to about 32 dmm.

The additional wax can exhibit a viscosity at 100° C. of greater than about 10 mm$^2$/s, alternatively greater than about 13 mm$^2$/s, alternatively from about 13 to about 18 mm$^2$/s. Preferably, the viscosity at 100° C. can be about 15 to about 16 mm$^2$/s. Viscosity can be measured according to ASTM D 445 (May 2017).

The additional wax can have an average hydrocarbon chain length of C32 to C35, preferably C32. Without being limited by theory, it is believed that an additional wax with an average chain length of from about C32 to C35 can increase the firmness of the personal care composition without significantly disrupting vapor release. It is preferred that the additional wax and petrolatum have a similar carbon chain distribution. Chain length can be measured using gas chromatography with flame ionization detection.

Non-limiting examples of suitable microcrystalline waxes can include Rajwax® MCW C72 (commercially available from Raj Petro Specialties P. Ltd., Mumbai, India), Multiwax® X-145 AH (commercially available from Sonneborn, Parsippany, N.J.), Witcovar® 146 (commercially available from Sonneborn), Multiwax® 7545 (commercially available from Sonneborn), Paracera™ MW (commercially available from Paramelt, Heerhugowaard, Netherlands), and combinations thereof.

The paraffin wax can be any grade of paraffin wax recognized in the art as suitable for human application. Non-limiting examples of paraffin wax can include white paraffin wax Kahlwax® 7366 (commercially available from Kahlwax®, Trittau, Germany), Carisma 57 Flex (commercially available from Alpha wax, Alphen aan den Rijn, Netherlands), and combinations thereof.

In one aspect, the additional wax can be a mixture of paraffin wax and a microcrystalline wax having a needle penetration at 25° C. of from about 35 to about 75 dmm, for instance, Rajell® WP456 (commercially available from Raj Petro Specialties P. Ltd.).

Without being limited by theory, it is believed that the additional wax can help in the formation of the internal structure of the personal care composition, forming a scaffold, or backbone, of the solid petrolatum into which droplets of the olfactory composition can be incorporated. This can result in a mixture resembling a 2-phase colloidal gel. It is believed that the additional microcrystalline wax can aid in olfactory composition retention and petrolatum crystallization, which may allow for an increased amount of olfactory composition to be retained in the petrolatum.

The personal care composition can comprise from about 2.5% to about 30% additional wax. Alternatively, the personal care composition can comprise from about 2.5% to about 20%, alternatively about 3 to about 15%, alternatively from about 4% to about 12.5%, alternatively from about 5% to about 10%, all by weight of the composition. Preferably, the personal care composition can comprise about 5% additional wax. The personal care composition can comprise less than about 20% additional wax, alternatively less than about 15% additional wax, alternatively less than about 12% additional wax, alternatively less than about 10% additional wax. The personal care composition can comprise from about 1% to about 8% of an additional wax, preferably from about 2.5% to about 5%, all by weight of the composition. One advantage to including an additional wax in a personal care composition comprising greater than about 20% olfactory composition is that it can provide a texture that is acceptable to consumers without significantly disrupting vapor release.

It was found that an additional wax, specifically a microcrystalline wax having a needle penetration at 25° C. of from about 35 to about 75 dmm, preferably about 41 dmm and more preferably about 60 dmm, can help reduce the oiliness or greasiness of a personal care composition comprising greater than about 20% olfactory composition by increasing the firmness without reducing the vapor release. It was also found that an additional microcrystalline wax having a needle penetration at 25° C. of from about 20 to about 34 dmm, preferably from about 22 to about 32 dmm, can help reduce the oiliness or greasiness of a personal care composition comprising greater than about 20% olfactory composition by increasing the firmness without reducing the vapor release. It was found that an additional microcrystalline wax having a needle penetration at 25° C. of from about 20 to about 34 dmm resulted in a firmer personal care composition as compared to compositions comprising an additional microcrystalline wax having a needle penetration at 25° C. of from about 35 dmm to about 75 dmm.

In one aspect, additional wax can be used to control the skin feel of the composition. In one aspect, additional wax can increase physical stability and help reduce the separation of the olfactory composition from the petrolatum.

In one aspect, the personal care composition can comprise a weight ratio of additional wax to olfactory composition of from about 1:1 to about 1:10, alternatively from about 1:3 to about 1:6.

In one aspect, the personal care composition can comprise a weight ratio of additional wax to petrolatum of from about 1:3 to about 1:15, alternatively from about 1:6 to about 1:13.

Olfactory Composition

The personal care composition can an olfactory composition comprising one or more olfactory agents. Non-limiting examples of olfactory agents can include cedar leaf oil, menthol, levomenthol, camphor, eucalyptus oil, cedar wood oil, turpentine, thymol, anethole, coriander, mandarin, petitgrain, armoise, cumin nitrile, marjoram sweet, pink pepper, basil, frankincense, methyl salicylate, rosemary oil, bergamot, galbanum, neroli, sichuan pepper, black pepper, grapefruit, nutmeg oil, tea tree oil, cardamom, jasmine, oil of black pepper, verveine, chinese ginger oil, lavender oil, orange sweet, vetivert, cinnamon leaf, lavendine, palmarosa, violet leaves, clary sage, lemongrass, patchouli oil, ylang, clove, lime, peppermint oil, olbus oil, and combinations thereof.

In one aspect, the olfactory agent can be selected from the group consisting of levomenthol, camphor, eucalyptus oil, cedar wood oil, turpentine oil, thymol, lavender oil, rosemary oil, peppermint oil, cardamom, ginger, petitgrain, nutmeg oil, cedar leaf oil, and combinations thereof.

In one aspect, the olfactory agent can be selected from the group consisting of levomenthol, camphor, eucalyptus oil, cedar wood oil, turpentine oil, thymol, cardamom, ginger, and combinations thereof.

In one aspect, the olfactory agent can be selected from the group consisting of levomenthol, camphor, eucalyptus oil, cedar wood oil, turpentine oil, thymol, cardamom, petitgrain oil, nutmeg oil, and combinations thereof.

The personal care composition can comprise from about 10% to about 50% of an olfactory composition, by weight of the composition, alternatively from about 15% to about 45%, alternatively from about 20% to about 40%, alternatively from about 22% to about 35%. In one aspect, the personal care composition can comprise from about 35% to about 50% of an olfactory composition. In one aspect, the personal care composition can comprise greater than about 20% of an olfactory composition, by weight of the composition, alternatively greater than about 25%, alternatively greater than about 30%. It was surprisingly found that if the personal care composition does not have greater than about 20% of an olfactory composition, the gelling agent may not able to significantly improve vapor release. Without being limited by theory, it is believed that vapor release is not significantly improved because there are not enough olfactory agents available in the composition to change the structure sufficiently to allow diffusion to the surface and thus maintain a constant vapor release over an 8-hour time of use.

Exemplary olfactory agents and the preferred ranges suitable for use in the personal care composition described herein are described in the table below

| Ingredient | Preferred Range Wt % | More Preferred Range Wt % | Most Preferred Range Wt % |
|---|---|---|---|
| Levomenthol | About 1 to about 15% | About 3 to about 12% | About 5 to about 11% |
| Camphor | About 1 to about 10% | About 2.5 to about 6% | About 4 to about 5.5% |
| *Eucalyptus* Oil | About 1 to about 10% | About 2 to about 8% | About 3 to about 6% |
| Cedarwood Oil | About 0.1 to about 5% | About 0.3 to about 3% | About 0.4 to about 1% |
| Turpentine Oil | About 1 to about 10% | About 2.5 to about 9% | About 4 to about 6% |
| Thymol | About 0.1 to about 5% | About 0.25 to about 2.5% | About 0.3 to about 1% |
| Nutmeg oil | About 0.3 to about 2% | About 0.4 to about 1.5% | About 0.4 to about 0.7% |
| Petritgrain Oil | About 0.5 to about 5% | About 1 to about 3% | About 1.5 to about 2% |
| Cardamom | About 0.25 to about 5% | About 0.3 to about 3% | About 0.5 to about 2% |

Sensory Agents

The personal care composition can comprise one or more sensory agents. Non-limiting examples of sensory agents can include cooling sensates, warming sensates, tingling sensates, sensory enhancers, and combinations thereof. Non-limiting examples of cooling sensates can include (1R, 2S, 5R)—N-(2-((R)-2aminopropanamido)-2-phenylethyl)-2-isopropyl-5-methylcyclohexane-1-carboxamide, 3-(1-methoxy)-propane-1,2-diol known as TK-10, isopulegol (under the tradename Coolact® P) and ρ-menthane-3,8-diol (under the tradename Coolact® 38D), icilin, menthoxypropanediol (under the trade name Coolact® 10), and combinations thereof. Non-limiting examples of warming sensates can include vanillyl alcohol n-butyl ether (sold as TK-1000 by Takasago International), vanillyl butyl ether (commercially available as HotFlux® from Corum, Inc., Taipei, Taiwan), capsaicin, nonivamide, ginger, and combinations thereof. Non-limiting examples of tingling sensates can include sichuan pepper, hydroxy alpha sanshool, jambu extracts, spilanthol, and combinations thereof, and combinations thereof. A suitable sensory enhancer can include a neuro-soother such as Mariliance™ available from Givaudan, Vernier, Switzerland.

One advantage to including sensory agents is that they can provide a topical sensory effect. When the personal care composition having one or more sensory agents is applied to the skin it can provide an on-skin sensation that can work in unison with the smell to provide an increased perception of product strength.

The personal care composition can comprise from about 0.001% to about 1.5% of a sensory agent, alternatively from about 0.01% to about 1%, alternatively from about 0.1% to about 0.75%, alternatively from about 0.2% to about 0.5%, all by weight of the composition.

Actives

The personal care composition may further comprise active ingredients. Suitable active ingredients include skin benefit agents, analgesics, antipyretic, anti-inflammatory agents, anesthetics and mixtures thereof. The personal care composition can comprise from about 0.01% to about 20% active ingredients, by weight of the composition, alternatively from about 0.1% to about 15%, alternatively from about 0.5% to about 10%, alternatively from about 1% to about 5%.

Analgesic, antipyretic and anti-inflammatory agents useful herein can include acetaminophen, aspirin, diclofenac, diflunisal, etodolac, fenoprofen, flurbiprofen, ibuprofen, ketoprofen, ketorolac, nabumetone, naproxen, piroxicam, caffeine, eugenol, or mixtures thereof. Local anesthetics useful herein include lidocaine, benzocaine, phenol, dyclonine, benzonotate, and mixtures thereof.

Skin benefit agents useful herein can include sunscreening agents such as 2-ethylhexyl p-methoxycinnamate, 2-ethylhexyl N,N-dimethyl-p-aminobenzoate, p-aminobenzoic acid, 2-phenylbenzimidazole-5-sulfonic acid, octocrylene, oxybenzone, homomenthyl salicylate, octyl salicylate, 4,4'-methoxy-t-butyldibenzoylmethane, 4-isopropyl dibenzoylmethane, 3-benzylidene camphor, titanium dioxide, zinc oxide, iron oxide, vitamin $B_3$ compounds, humectants, amino acids, vitamin C compounds, panthenol and derivatives, vitamin E and its derivatives, salicylic acid and other beta-hydroxy acids, aloe vera oil, and mixtures thereof.

Additional Fragrance Materials

The personal care composition may further comprise additional fragrance materials that are acceptable to consumers. In one example, fragrance materials suitable for use herein can include cajeput oil, fennel oil, geranium oil, lemon oil, spearmint oil, myrtle oil, oregano oil, pine oil, sarriette oil, thyme oil, and mixtures thereof. In one aspect, additional fragrance materials may comprise the chemical constituents of essential oils such as vanillin, ethyl vanillin, musk, methyl-dihydrojasmonate, anethol, catechol, camphene, ferulic acid, farnesol, hinokitiol, tropolone, menthol, methyl salicylate, carvacol, terpineol, verbenone, ratanhia extract, caryophyllene oxide, citronella acid, curcumin, nerolidol, or mixtures thereof. These materials may be used at levels and ratios known to those skilled in the art of mixing fragrance materials for personal care compositions, whilst maintaining the levels of base scent coming from the levomenthol, camphor, eucalyptus oil, cedar wood oil, cedar leaf oil, nutmeg, turpentine, and/or thymol.

In one aspect, the personal care composition described herein can have a vapor release of from about 30 mg to about 80 mg after 3 hours at 35° C., alternatively from about 35 mg to about 50 mg, alternatively from about 38 mg to about 45 mg. In one aspect, the personal care composition described herein can have a vapor release of from about 30 mg to about 145 mg after 3 hours at 35° C., alternatively from about 35 mg to about 100 mg. In one aspect, the personal care composition described herein can have a vapor release of from about 80 mg to about 155 mg after 3 hours at 35° C. Vapor release can be measured according to the Mass Loss Measurement Method described hereafter.

In one aspect, the personal care composition described herein can have a vapor release of from about 35 mg to about 300 mg after 8 hours at 35° C., alternatively from about 45 mg to about 250 mg, alternatively from about 55 mg to about 230 mg, alternatively from about 58 mg to about 150 mg, alternatively from about 50 mg to about 65 mg. The personal care composition can have a vapor release of greater than about 35 mg after 8 hours at 35° C., alternatively greater than about 50 mg alternatively greater than about 55 mg, alternatively greater than about 60 mg.

The personal care composition can have a vapor release of from about 65 mg to about 90 mg after 16 hours at 35° C., alternatively from about 68 mg to about 85 mg, alternatively from about 60 mg to about 65 mg. The personal care composition can have a vapor release of greater than about 65 mg after 16 hours at 35° C. The personal care composition can have a vapor release of from about 150 mg to about 450 mg after 16 hours at 35° C., alternatively from about 175 mg to about 380 mg, alternatively from about 200 mg to about 370 mg, alternatively from about 250 mg to about 320 mg.

The personal care composition can have an Instability Index value of from about 0.10 to about 0.80, alternatively from about 0.30 to about 0.70, alternatively from about 0.50 to about 0.60. Alternatively, the personal care composition can have an Instability Index value of less than about 1.0, preferably less than about 0.9, more preferably less than about 0.75. The personal care composition can have an Instability Index of less than about 0.6, alternatively less than about 0.5, alternatively less than about 0.4, alternatively less than about 0.2. The Instability Index value can be measured according to the Instability Test Method described hereafter. It is believed that the Instability Index value can be used as a measure of physical stability. The more prone a sample is to phase separation, the higher the Instability Index value will be.

The personal care composition can have a Firmness Parameter at the time of production of from about 93 to about 185 g·sec, alternatively from about 95 to about 165 g·gec, alternatively from about 98 to about 160 g·sec, alternatively from about 100 to about 150 g·gec. The Firmness Parameter can be measured according to the Texture Analysis Test Method described hereafter.

The personal care composition may be in any form suitable for consumer use. In one aspect, the personal care composition may be formulated as a leave-on composition or a rinse-off composition. As used herein, "leave-on composition" includes compositions that are intended to be applied to a bodily surface of a consumer such as the skin or hair and maintained on the surface for a prolonged time, such as at least 5 minutes or alternatively at least 30 minutes, without being actively removed by washing, rinsing, wiping, rubbing or other forms of mechanical removal. As used herein, "rinse-off composition" includes compositions that are intended to be applied to a bodily surface of a consumer, such as the skin or hair, and subsequently removed by washing, rinsing, wiping, rubbing or other forms of mechanical removal within less than 5 minutes of application. In one aspect, the personal care composition is a leave-on composition.

The personal care composition may be formulated as a lotion, an aerosol, a cream, a gel, a liquid, a viscous liquid, or a paste. In one example, the personal care composition can be in the form of a patch that can be applied to the user's body or clothing. Preferably, such patches comprise an adhesive layer that enables attachment to the user's body or clothing. As used herein, "liquid" includes compositions having a viscosity of less than 10 mPa·s at 25° C. As used herein, "viscous liquid" means a liquid composition that has a viscosity of from about 10 mPa·s to about 300000 mPa·s when measured at 25° C., alternatively from 50 mPa·s to 150 000 mPa·s. Viscosity herein is measured using a Brookfield RVT, T-C Spindle at 5 rpms and Heliopath Stand. Viscous liquid compositions have a viscosity that is greater than that of water, and typically provide improved application characteristics when compared with products having a viscosity similar to that of water when applied directly by the user by hand. In one aspect, the personal care composition is in a form selected from the group consisting of a viscous liquid, a gel, a paste, and combinations thereof.

In one aspect, the personal care composition can provide at least temporarily cough suppression due to minor throat and bronchial irritation such as associated with the common cold. In one aspect, the personal care composition can provide at least temporarily relief of minor aches and/or pains of muscles and/or joints. In one aspect, the personal care composition can provide relief of nasal congestion.

The personal care composition can be applied to the skin of a user on the throat, forehead, and chest. The user can place a desired amount of the personal care composition on his or her skin and rub it in for about 5 seconds to about 3 minutes, alternatively for about 20 seconds to about 90 seconds, alternatively for about 30 seconds to about 60 seconds. In one example, the personal care composition can be covered with a warm, dry cloth after application to the skin.

A dose of the personal care composition can comprise from about 0.5 g to about 10 g, alternatively from about 1 g to about 8 g, alternatively from about 1.5 g to about 6 g, alternatively from about 3 g to about 4.5 g, alternatively about 7.5 g.

The personal care composition can be used one time per day or multiple times per day. A dose of the personal care composition can be applied to the skin and/or clothing up to three times per day. In another example, a dose of the personal care composition can be applied to the skin up to four times per day. In one example, the personal care composition can be used as directed by a physician. The personal care composition can be applied to the skin and/or clothing on a daily basis or only as needed. Another aspect of the present invention includes a method of providing one or more health benefits by administering the personal care composition to a user in need thereof. As used herein, the one or more health benefits may be selected from the group consisting of providing relief of nasal congestion, suppressing a cough, providing relief of muscle aches and pain, improving the quality of sleep to a user suffering from a cold or flu, topical analgesic effects, and combinations thereof.

EXAMPLES AND DATA

The following data and examples, including comparative examples, are provided to help illustrate personal care compositions described herein. The exemplified compositions are given solely for the purpose of illustration and are not to be construed as limitations of the present invention, as many variations thereof are possible without departing from the spirit and scope of the invention. All parts, percentages, and ratios herein are by weight unless otherwise specified.

Microcrystalline Wax Test

Formulas were prepared to assess the impact of additional microcrystalline waxes on the texture, vapor release, and physical stability of a personal care composition having an increased olfactory agent content. Examples A-N were prepared as described hereinafter. Examples A and B are controls containing no additional microcrystalline wax. Examples C-F and G-H illustrate personal care compositions containing an added microcrystalline wax exhibiting a needle penetration at 25° C. of from about 35 to about 75 dmm. Examples I and J are comparative examples containing an additional microcrystalline wax exhibiting a needle penetration at 25° C. of about 14 to about 19 dmm. Examples K and L illustrate personal care compositions containing an additional microcrystalline wax exhibiting a needle penetration at 25° C. of about 20 to about 34 dmm. Example M illustrates a comparative example containing a gelling agent and solvent. Examples N and O illustrate personal care compositions comprising a gelling agent, solvent, and an additional microcrystalline wax. The Examples presented in the tables below were not tested at the same time; however, the data are shown together for ease of comparison.

Examples A-O were made according to the formulas in Table 1.

The table below shows the Firmness Parameter, average vapor release, and Instability Index for each example. The Firmness Parameter was measured according to the Texture Test Method described hereafter. Instability Index was measured according to the Instability Index Test Method described hereafter. Vapor release was measured according to the Vapor Release Test Method described hereafter. Vapor release was measured at various points over a 16-hour time period. Vapor release is recorded in Table 1 as the average mass loss (mg) measured at 3 hours and 8 hours, or the average calculated mass loss (mg) at 8 hours if the measurement was not performed at this timepoint.

The calculated mass loss at 8 hours was determined by the following equation, estimating diffusion through a medium with respect to time and space:

$$M = k\left(l - \left(\operatorname{Ierf}(\alpha\, l) + \frac{1}{\alpha\sqrt{\pi}}\exp(-\alpha^2 l^2) - \frac{1}{\alpha\sqrt{\pi}}\right)\right)$$

Where M is predicted mass loss (mg), l is sample thickness, k is the total amount of olfactory composition available to be released as time approaches infinity, where $\alpha = \beta \times \sqrt{t}$ where t is time (min) and $\beta$ is the coefficient proportional to the diffusivity. Using a mathematical algorithm, we found the values of $\beta$ and k that fit a particular vapor release profile, which enabled us to calculate M at 480 min (8 hours). It is noted that sample thickness ("l") was fixed at 1 for comparison as sample thickness was considered constant. In addition, area and temperature were considered constant.

TABLE 1

| | EX. A 1x Control Wt % | EX. B 2x Control Wt % | EX. C Wt % | EX. D Wt % | EX. E Wt % | EX. F Wt % | EX. G Wt % | EX. H Wt % |
|---|---|---|---|---|---|---|---|---|
| Petrolatum[1] | 83.76 | 70.04 | 65.02 | 60.09 | 50.15 | 39.99 | 65.28 | 60.06 |
| Olfactory Composition | 16.24 | 29.96 | 29.98 | 28.89 | 29.91 | 29.95 | 29.72 | 29.97 |
| Raj Wax® C72[2] | 0 | 0 | 5.0 | 10.02 | 19.94 | 30.07 | 0 | 0 |
| Multiwax® X-145 AH[3] | 0 | 0 | 0 | 0 | 0 | 0 | 5.0 | 9.97 |
| Paracera™ M[4] | 0 | 0 | 0 | 0 | 0 | 0 | 0 | 0 |
| Paracera™ MW[5] | 0 | 0 | 0 | 0 | 0 | 0 | 0 | 0 |
| Avg Vapor Release 3 hrs (mg) | 26.1 | 38.0 | 42.5 | 42.4 | 39.7 | 35.8 | 42.3 | 43.1 |
| Avg Vapor Release 8 hrs (mg) | 38.7 | 59.5 | 62.4 | 59.2 | 49.8 | 42.8 | 55.4 | 55.1 |
| Firmness Parameter (g · sec) | 141.06 | 68.50 | 93.45 | 157.00 | 238.50 | 313.87 | 119.74 | 131.69 |
| Instability Index | 0.40 | 0.90 | 0.80 | 0.62 | 0.58 | 0.54 | 0.48 | 0.52 |

[1]V30 Snow white (sold by Sonneborn, Amsterdam, Netherlands).
[2]RajWax® C72 (sold by Raj Petro Specialties P. Ltd., Mumbai, India).
[3]Multiwax® X-145 AH (sold by Sonneborn, Parsippany, NJ).
[4]Paracera™ M (sold by Paramelt, Heerhugowaard, Netherlands).
[5]Paracera™ MW (sold by Paramelt, Heerhugowaard, Netherlands)

| | EX. I Wt % | EX. J Wt % | EX. K Wt % | EX. L Wt % | EX. M Wt % | EX. N Wt % | EX. O Wt % |
|---|---|---|---|---|---|---|---|
| Petrolatum[1] | 65.08 | 59.97 | 65.04 | 60.12 | 67.56 | 62.55 | 57.57 |
| Olfactory Composition | 29.92 | 30.02 | 29.96 | 29.87 | 29.9 | 29.9 | 29.92 |

-continued

|  | EX. I Wt % | EX. J Wt % | EX. K Wt % | EX. L Wt % | EX. M Wt % | EX. N Wt % | EX. O Wt % |
|---|---|---|---|---|---|---|---|
| Raj Wax® C72[2] | 0 | 0 | 0 | 0 | 0 | 5.05 | 10.02 |
| Multiwax® X-145 AH[3] | 0 | 0 | 0 | 0 | 0 | 0 | 0 |
| Paracera™ M[4] | 5.00 | 10.01 | 0 | 0 | 0 | 0 | 0 |
| Paracera™ MW[5] | 0 | 0 | 5.00 | 10.01 | 0 | 0 | 0 |
| Dibutyl ethylhexanoyl glutamide "EB-21" | 0 | 0 | 0 | 0 | 0.20 | 0.20 | 0.20 |
| Dibutyl lauroyl glutamide "GP-1" | 0 | 0 | 0 | 0 | 0.31 | 0.30 | 0.30 |
| 3-methyl-1,3-butanediol | 0 | 0 | 0 | 0 | 2.03 | 2.00 | 1.99 |
| Avg Vapor Release 3 hrs (mg) | 36.3 | 32.7 | 54.27 | 54.07 | 136.90 | 152.47 | 133.27 |
| Avg Vapor Release 8 hrs (mg) | 47.4 | 43.1 | 72.46 | 83.89 | 225.70 | 225.37 | 218.03 |
| Firmness Parameter (g·sec) | 168.98 | 295.40 | 177.26 | 182.21 | 98.42 | 164.77 | 228.02 |
| Instability Index | 0.58 | 0.45 | 0.60 | 0.67 | 0.68 | 0.14 | 0.21 |

[1]V30 Snow white (sold by Sonneborn, Amsterdam, Netherlands)
[2]RajWax® C72 (sold by Raj Petro Specialties P. Ltd., Mumbai, India).
[3]Multiwax® X-145 AH (sold by Sonneborn, Parsippany, NJ).
[4]Paracera™ M (sold by Paramelt, Heerhugowaard, Netherlands).
[5]Paracera™ MW (sold by Paramelt, Heerhugowaard, Netherlands).

It was found that as the total olfactory composition level increased, the firmness and physical stability of the composition decreased (i.e. the Instability Index increased). Example A ("1× Control"), which had 16.24% olfactory composition and no additional microcrystalline wax, had a Firmness Parameter of 141.06 g·sec and an Instability Index of 0.40. When the level of olfactory composition was increased to 29.96% in Example B ("2× Control") the Texture Parameter decreased to 68.50 g·sec and the Instability Index increased to 0.90, indicating that the formulation had decreased physical stability. It is believed that consumers may find a personal care composition having a Texture Parameter of about 68 g·sec to have an unacceptable soft and/or greasy texture.

It was surprisingly found that the addition of certain microcrystalline waxes was able to increase the firmness of the personal care composition without disrupting vapor release.

Examples C-F contained RajWax® C72, a microcrystalline wax exhibiting a needle penetration at 25° C. of from about 35 to about 75 dmm. When 5% (Example C) and 10% (Example D) RajWax® C72 was added to the composition, the Firmness Parameter increased to an acceptable level and the Instability Index decreased as compared to the 2× Control, while the average vapor release remained similar to the 2× Control. Despite hardening the composition, the added microcrystalline wax in Examples C and D did not hinder the vapor release. However, at about 20% and 30% RajWax® C72, as in Examples E and F, the Firmness Parameter increased to over 238 g·sec and the average vapor release at 8 hours decreased to levels significantly lower than the 2× Control.

Examples G and H contained Multiwax® X-145 AH, a second microcrystalline wax exhibiting a needle penetration at 25° C. of from about 35 to about 75 dmm. When 5% (Example G) and 10% (Example H) Multiwax® X-145 AH was added to the composition, the Firmness Parameter increased to an acceptable level and the Instability Index decreased as compared to the 2× Control, while the average vapor release remained similar to the 2× Control. Despite hardening the composition, the added microcrystalline wax in Examples G and H did not significantly hinder the vapor release.

Examples K and L contained Paracera™ MW Wax, a microcrystalline wax exhibiting a needle penetration at 25° C. of about 20 to about 34 dmm. When Paracera™ MW Wax was added in Examples K and L, physical stability and average vapor release improved and the Firmness Parameter increased to 177.26 g·sec and 182.21 g·sec, respectively. It is believed that in some geographies, a Firmness Parameter at this level may be unacceptable to some consumers; however, in other geographies it may be acceptable and/or preferred to have a firmer texture.

It was surprisingly found that the addition of some microcrystalline waxes significantly disrupted vapor release and/or increased the firmness of the composition to a level that is believed to be unacceptable to consumers for a topical application. Examples I and J contained Paracera™ M wax, a microcrystalline wax exhibiting a needle penetration at 25° C. of about 14 to about 19 dmm. When Paracera™ M Wax was added in Examples I and J, physical stability improved; however, the average vapor release at 3 and 8 hours for Examples I and J decreased to levels similar to the 1× Control.

The impact of additional wax in a personal care composition comprising a gelling agent mixture was also evaluated. Example M, which contained 0.51% gelling agent (EB-21+GP-1) and 2.03% 3-methyl-1,3-butanediol solvent, had a vapor release of 225.70 mg at 8 hours, more than 3× greater than the 2× Control, and had a Firmness Parameter of 98.42 g·sec. An improvement in the Instability Index was also observed. Example N, which contained 0.50% gelling agent (EB-21+GP-1) in 3-methyl-1,3-butanediol solvent and 5.05% RajWax® C72, had an average vapor release of 225.37 mg at 8 hours. Example N had a Firmness Parameter of 164.77 g·sec and an Instability Index of 0.14. It was surprisingly found that the additional microcrystalline wax in this formula was able to improve the texture and physical stability without disrupting vapor release when added in combination with the gelling agent mixture. When 5% Rajwax® C72 was added, as in Example C, the Instability Index decreased to 0.80. When the gelling agent mixture was added, as in Example M, the Instability index decreased to 0.68. However, when 5% Rajwax® C72 and the gelling agent mixture were added, as in Example N, the Instability Index surprisingly decreased to 0.14. Without being limited by theory, it is believed there is a synergy between the additional microcrystalline wax and gelling agent mixture which improves physical stability.

It was found that at about 10% RajWax® C72, while the vapor release was not significantly impacted, the firmness increased to a level that may not be acceptable to consumers. Example O, which contained 0.5% gelling agent mixture (EB-21+GP-1) and 10.02% RajWax® C72, had an average vapor release of 218.03 mg at 8 hours, a Firmness Parameter of 228.02 g·sec, and an Instability Index of 0.21.

Examples A-B were made according to the following procedure:

First, a water bath (an IKA® Werke LT6, IKA®, Wilmington, N.C., or equivalent) is connected to a main reactor vessel (IKA® Werke LR-2000V Lab Reactor, IKA®, or equivalent) and the water bath is set to 60.0° C. Petrolatum is measured and transferred using a spatula into the main reactor vessel. The petrolatum is back-weighed to ensure accurate addition. Then, the lid is lowered, and the stirrer is set to 60 RPM. The vessel is heated with a jacket set point temperature of 60.0° C. (corresponding to a reactor vessel temperature of 60±1° C.) until the mixture is fully melted.

While the main reactor vessel is mixing, a premix of olfactory agents is prepared. First, camphor and thymol are added to the premix beaker. Menthol crystals are ground up with a pestle and mortar and then added to the premix beaker. In order, turpentine oil, eucalyptus oil, and cedar wood oil are added to the premix beaker. A magnetic stir bar is inserted into the premix beaker and the beaker is then covered with parafilm to minimize evaporative losses. The premix is stirred at sufficient speed to induce mixing without creating a vortex. The premix is mixed until it becomes clear in color and no visible particles remain.

Once the premix is prepared, the main reactor vessel is cooled with a water bath set point of 51.0° C. (corresponding to a reactor vessel temperature of 51±1° C.). Once the reactor vessel temperature is stabilized at 51° C., the water bath temperature is turned up to 56.2° C. Then, one of the large stoppers in the lid is immediately removed. The stir bar is removed from the premix vessel and the premix is slowly added to the main reactor vessel through the opening to form a final mixture. The reactor temperature is monitored to ensure that it does not fall outside the allowed range (51±1° C.). The stopper is then replaced to minimize evaporative loss.

The final mixture is mixed for 30 minutes at 60 RPM with a water bath temperature of 51° C. (reactor vessel temperature of 51±1° C.). The water bath temperature is then cooled to 45° C. (reactor vessel temperature of 45±1° C.) whilst stirring at 60 rpm. Once the temperature is stabilized, the water bath temperature is set to 47° C. and the tap is opened fully to begin dispensing into jars. The jars are covered with a lid and cooled in a refrigerator for 10 minutes. After removal from the refrigerator, the lid on the jar is sealed. The reactor vessel is then removed and cleaned. The jars are stored at ambient temperature.

Examples C-L were made according to the following procedure:

First, a water bath (an IKA® Werke LT6, IKA®, Wilmington, N.C., or equivalent) is connected to a main reactor vessel (IKA® Werke LR-2000V Lab Reactor, IKA®, or equivalent) and the water bath is set to 85.0° C. Petrolatum and additional wax are measured and transferred using a spatula into the main reactor vessel. The petrolatum and additional wax are back-weighed to ensure accurate addition. Then, the lid is lowered, and the stirrer is set to 60 RPM. The vessel is heated with a jacket set point temperature of 85.0° C. (corresponding to a reactor vessel temperature of 85±1° C.) until the mixture is fully melted.

While the main reactor vessel is mixing, a premix of olfactory agents is prepared. First, camphor and thymol are added to the premix beaker. Menthol crystals are ground up with a pestle and mortar and then added to the premix beaker. In order, turpentine oil, eucalyptus oil, and cedar wood oil are added to the premix beaker. A magnetic stir bar is inserted into the premix beaker and the beaker is then covered with parafilm to minimize evaporative losses. The premix is stirred at sufficient speed to induce mixing without creating a vortex. The premix is mixed until it becomes clear in color and no visible particles remain.

Once the premix is prepared, the main reactor vessel is cooled with a water bath set point of 51.0° C. (corresponding to a reactor vessel temperature of 51±1° C.). Once the reactor vessel temperature is stabilized at 51° C., the water bath temperature is turned up to 56.2° C. Then, one of the large stoppers in the lid is immediately removed. The stir bar is removed from the premix vessel and the premix is slowly added to the main reactor vessel through the opening to form a final mixture. The reactor temperature is monitored to ensure that it does not fall outside the allowed range (51±1° C.). The stopper is then replaced to minimize evaporative loss.

The final mixture is mixed for 30 minutes at 60 RPM with a water bath temperature of 51° C. (reactor vessel temperature of 51±1° C.). The water bath temperature is then cooled to 45° C. (reactor vessel temperature of 45±1° C.) whilst stirring at 60 rpm. Once the temperature is stabilized, the water bath temperature is set to 47° C. and the tap is opened fully to begin dispensing into jars. The jars are covered with a lid and cooled in a refrigerator for 10 minutes. After removal from the refrigerator, the lid on the jar is sealed. The reactor vessel is then removed and cleaned. The jars are stored at ambient temperature.

Examples M was made according to the following procedure:

First, a water bath (an IKA® Werke LT6, IKA®, Wilmington, N.C., or equivalent) is connected to a main reactor vessel (IKA® Werke LR-2000V Lab Reactor, IKA®, or equivalent) and the water bath is set to 60.0° C. Petrolatum is measured and transferred using a spatula into the main reactor vessel. The petrolatum is back-weighed to ensure accurate addition. Then, the lid is lowered, and the stirrer is set to 60 RPM. The vessel was heated with a jacket set point temperature of 60.0° C. (corresponding to a reactor vessel temperature of 60±1° C.) until the mixture is fully melted.

On a separate hot plate, EB-21, GP-1 and 3-methyl-1,3-butanediol are added to a secondary vessel and agitated to induce a vortex. The mixture is heated to 95-100° C. with stirring using a magnetic flea until fully transparent, with no visible particles to form a gelling agent mixture.

When both the main reactor vessel and the secondary vessel are homogeneous and have reached their target temperature, the secondary vessel is cooled to 75° C. Then, the magnetic flea is removed, and the gelling agent mixture is poured from the secondary vessel into the main reactor vessel. The initial and final weights of the gelling agent mixture are recorded.

While the main reactor vessel is mixing, a premix of olfactory agents is prepared. First, camphor and thymol are added to the premix beaker. Menthol crystals are ground up with a pestle and mortar and then added to the premix beaker. In order, turpentine oil, eucalyptus oil, and cedar wood oil are added to the premix beaker. A magnetic stir bar is inserted into the premix beaker and the beaker is then covered with parafilm to minimize evaporative losses. The premix is stirred at sufficient speed to induce mixing without creating a vortex. The premix is mixed until it becomes clear in color and no visible particles remain.

Once the premix is prepared, the main reactor vessel is cooled with a water bath set point of 51.0° C. (corresponding to a reactor vessel temperature of 51±1° C.). Once the reactor vessel temperature is stabilized at 51° C., the water bath temperature is turned up to 56.2° C. Then, one of the large stoppers in the lid is immediately removed. The stir bar is removed from the premix vessel and the premix is slowly added to the main reactor vessel through the opening to form a final mixture. The reactor temperature is monitored to ensure that it does not fall outside the allowed range (51±1° C.). The stopper is then replaced to minimize evaporative loss.

The final mixture is mixed for 30 minutes at 60 RPM with a water bath temperature of 51° C. (reactor vessel temperature of 51±1° C.) The water bath temperature is then cooled to 45° C. (reactor vessel temperature of 45±1° C.) whilst stirring at 60 rpm. Once the temperature is stabilized, the water bath temperature is set to 47° C. and the tap is opened fully to begin dispensing into jars. The jars are covered with a lid and cooled in a refrigerator for 10 minutes. After removal from the refrigerator, the lid on the jar is sealed. The reactor vessel is then removed and cleaned. The jars are stored at ambient temperature.

Examples N-O were made according to the following procedure

First, a water bath (an IKA® Werke LT6, IKA®, Wilmington, N.C., or equivalent) is connected to a main reactor vessel (IKA® Werke LR-2000V Lab Reactor, IKA®, or equivalent) and the water bath is set to 85.0° C. Petrolatum and wax are measured and transferred using a spatula into the main reactor vessel. The petrolatum and wax is back-weighed to ensure accurate addition. Then, the lid is lowered, and the stirrer is set to 60 RPM. The vessel is heated with a jacket set point temperature of 85.0° C. (corresponding to a reactor vessel temperature of 85±1° C.) until the mixture is fully melted.

On a separate hot plate, EB-21, GP-1 and 3-methyl-1,3-butanediol are added to a secondary vessel and agitated to induce a vortex. The mixture is heated to 95-100° C. with stirring using a magnetic flea until fully transparent, with no visible particles to form a gelling agent mixture.

When both the main reactor vessel and the secondary vessel are homogeneous and have reached their target temperature, the secondary vessel is cooled to 75° C. Then, the magnetic flea is removed and the gelling agent mixture is poured from the secondary vessel into the main reactor vessel. The initial and final weights of the gelling agent mixture are recorded.

While the main reactor vessel is mixing, a premix of olfactory agents is prepared. First, camphor and thymol are added to the premix beaker. Menthol crystals are ground up with a pestle and mortar and added to the premix beaker. In order, turpentine oil, eucalyptus oil, and cedar wood oil are added to the premix beaker. A magnetic stir bar is inserted into the premix beaker and the beaker is then covered with parafilm to minimize evaporative losses. The premix is stirred at sufficient speed to induce mixing without creating a vortex. The premix is mixed until it becomes clear in color and no visible particles remain.

Once the premix is prepared, the main reactor vessel is cooled with a water bath set point of 51.0° C. (corresponding to a reactor vessel temperature of 51±1° C.). Once the reactor vessel temperature is stabilized at 51° C., the water bath temperature is turned up to 56.2° C. Then, one of the large stoppers in the lid is immediately removed. The stir bar is removed from the premix vessel and the premix is slowly added through the opening to form a final mixture. The reactor temperature is monitored to ensure that it did not fall outside the allowed range (51±1° C.). The stopper is then replaced to minimize evaporative loss.

The final mixture was mixed for 30 minutes at 60 RPM with a water bath temperature of 51° C. (reactor vessel temperature of 51±1° C.) The water bath temperature is then cooled to 45° C. (reactor vessel temperature of 45±1° C.) whilst stirring at 60 rpm. Once the temperature is stabilized, the water bath temperature is set to 47° C. and the tap is opened fully to begin dispensing into jars. The jars are covered with a lid and cooled in a refrigerator for 10 minutes. After removal from the refrigerator, the lid on the jar is sealed. The reactor vessel is then removed and cleaned. The jars are stored at ambient temperature.

Instability Index Test Method

Instability analysis is carried out on the samples to establish relative potential for separation of the olfactory agent oils from the petrolatum material based on applied centrifugal forces. The result is an indication of syneresis. As the sample separates into its constituent petrolatum and oil phases, the larger the volume of the liquid layer, which results in a greater amount of light being transmitted. Thus, the more prone a sample is to phase separation, the more liquid separates during centrifuging, and the less stable the product is predicted to be.

The Instability Index Test Method is conducted as follows. A dispersion analyzer, such as a LUM LUMiSizer® (LUM GmbH, Berlin, Germany) or equivalent, is used in this method. The dispersion analyzer is interfaced with a personal computer loaded with the associated LUM software, SEPView, that collects and analyzes the data inputted from the instrument.

Preparation of Samples:

Samples are measured as received. A sample is removed from packaging or sample jar and immediately analyzed without first being equilibrated to the lab environment. The sample is mixed prior to dispensing to ensure homogeneity. The sample is filled into a 2 mL plastic syringe and filled into the sample vial from the base up. Care is taken to ensure that no gaps or air pockets are present in the sample. A suitable sample vial is a LUM polycarbonate cells 2 mm optical path (type 2), or equivalent.

Instrument Setup:
The dispersion analyzer is set to the following conditions.

| Test | Interval (sec) | Speed | Light Factor | Temperature |
|---|---|---|---|---|
| 1 (Sample Prep) | 135 | 4,000 rpm | 1.00 | 30.0° C. |
| 2 | 45 | 4,000 rpm | 1.00 | 30.0° C. |

To eliminate bubbles in the petrolatum and to allow the sample to settle, the vial is placed in the dispersion analyzer and centrifuged at 4,000 rpm for 135 seconds (maintained at 30° C.). No measurements are taken during this period.

Next, samples are centrifuged at 4,000 rpm for 12 hours (maintained at 30° C.) with constant measurement of the amount of light transmission.

The Instability Index is generated over the full run time of the experiment in the range from the meniscus of the sample to a point in the sample 10.0 mm below it. The Instability Index is calculated from the last measurement taken. Instability Index measures the percent of the sample that experienced separation in top 10.0 mm of the sample after centrifugation during 12 hours at 30° C.

Texture Analysis Test Method

The Texture Analysis Test Method is conducted as follows. A texture analyzer, such as a TA.XTplus Texture Analyzer (Stable Micro Systems, Godalming, Surrey, UK) or equivalent, is used in this method. The texture analyzer is interfaced with a personal computer loaded with Exponent data acquisition software that collects and analyzes the data inputted from the instrument.

The texture analyzer temperature control on the water bath is set to 35° C. and the instrument is calibrated according to manufacturer instructions. The texture analyzer is equipped with a male cone probe and a heavy-duty platform. The empty female cone holder is positioned on the heavy-duty platform and locked into place by tightening the screws. The male cone probe is moved down so that it fits into the female cone sample holder. When the male and female cones are practically touching, the heavy-duty platform is maneuvered so that the cones are precisely aligned, and the screws of the heavy-duty platform are tightened. The pre-set probe position is set to 25 mm. The texture analyzer is set to a return distance of 25 mm, a return speed of 10 mm/s, and a contact force of 1 g.

Samples are measured at the time of production, meaning immediately after production or within about 2 weeks after production. Prior to testing, samples are stored in sealed jars at room temperature (about 23° C.). The specimen is removed from the jar and is placed in the female cone, pressed down into the cone to eliminate air pockets, and excess specimen is scraped off with a spatula to leave a flat test area. The specimen is equilibrated to 35° C. before testing. Each test commences from the 25 mm start position. Each specimen is measured in triplicate and the average value is recorded as the work of shear in g·sec.

Mass Loss Measurement Method

The Mass Loss Measurement Method is conducted in a room set to a temperature of 21° C. The door to the room is kept closed when possible to keep airflow constant. The temperature of a water heated plate is set to 37.5° C. The plate is heated until the temperature at the center of the hot plate is between 33° C.±1° C. A protective wall is mounted around the water heated plate to minimize airflow.

Samples are measured as received. A sample is removed from packaging or sample jar and immediately analyzed without first being equilibrated to the lab environment. 3 foil squares of approximately 5 cm are cut and pre-weighed for each sample. An application template is prepared by cutting a 44 mm diameter circle out of a 1.5 mm thick sheet of plastic. The template is pushed down onto the foil to avoid gaps. Using a spatula, a sample is applied to the surface of the tin foil square inside the circle of the application template to fill the entire circle. Excess sample extruding from the circle is scraped off. If the surface of the sample is not flat and even with the top of the application template, additional sample is loaded into the circle and scraped until a uniform sample layer is created. The application template is removed from the tin foil whilst leaving the sample intact. The tin foil with the sample is weighed and the weight is recorded. The expected weight is from 1.7-2.0 g. The 44 mm circle is equivalent to a 15 $cm^2$ surface area.

The tin foil sample is immediately placed onto the center of the water heated plate and the time is recorded. The equipment (spatula, template, and scraper) are cleaned with paper towel in between samples. At time points 30 minutes, 1 hour, 2 hours, 3 hours, hours, the sample is removed from the water heated plate and is weighed on the same tared balance. The weight is recorded. The samples are tested in triplicate for each time point. By subtracting the weight of the foil from each reading and then the new weights from the previous weight, the weight loss over time is measured and the average of the weight loss is recorded.

Combinations

A. A personal care composition comprising: from 35% to 90% petrolatum, by weight of the composition, preferably from 50% to 85%, more preferably from 60% to 75%; an additional microcrystalline wax having a needle penetration at 25° C. of from 35 to 75 dmm; from 1% to 6% of a gelling agent mixture, by weight of the composition; and from 20% to 50% of an olfactory composition, by weight of the composition.

B. The personal care composition according to paragraph A comprising from 2.5 to 20%, by weight of the composition, of the additional microcrystalline wax, preferably from 3 to 15%, more preferably from 5 to 10%.

C. The personal care composition according to any of the preceding paragraphs wherein the gelling agent mixture comprises a gelling agent comprising dibutyl lauroyl glutamide and dibutyl ethylhexanoyl glutamide.

D. The personal care composition according any of the preceding paragraphs comprising from 2.5 to 5% of the gelling agent mixture, by weight of the composition.

E. The personal care composition according to any of the preceding paragraphs wherein the olfactory composition comprises an olfactory agent selected from the group consisting of levomenthol, camphor, eucalyptus oil, cedar wood oil, turpentine oil, thymol, lavender oil, rosemary oil, peppermint oil, cardamom, ginger, petitgrain, nutmeg oil, cedar leaf oil, and combinations thereof.

F. The personal care composition according to any of the preceding paragraphs wherein the additional microcrystalline wax has a drop melting point of from 60° C. to 77° C.

G. The personal care composition according to any of the preceding paragraphs wherein the additional microcrystalline wax has a needle penetration at 25° C. of from 40 to 60 dmm.

H. The personal care composition according to any of the preceding paragraphs wherein the personal care composition is in a form selected from the group consisting of a viscous liquid, a gel, a paste, and combinations thereof.

I. The personal care composition according to any of the preceding paragraphs wherein the personal care composition comprises a weight ratio of the additional microcrystalline wax to petrolatum of from 1:3 to 1:15.

J. The personal care composition according to any of the preceding paragraphs wherein the personal care composition has a vapor release of greater than 35 mg at 8 hours as measured by the Vapor Release Test Method.

K. The personal care composition according to any of the preceding paragraphs wherein the personal care composition has a vapor release of 35 mg to 300 mg at 8 hours as measured by the Vapor Release Test Method.

L. A method of suppressing a cough, the method comprising the step of administering a personal care composition to a user in need thereof; wherein the personal care composition comprises: from 35% to 90% petrolatum, by weight of the composition; an additional microcrystalline wax having a needle penetration at 25° C. of from 35 to 75 dmm; from 1% to 6% of a gelling agent mixture, by weight of the composition; and from 20% to 50% of an olfactory composition, by weight of the composition.

M. The method according to paragraph L comprising from 2.5 to 20%, by weight of the composition, of the additional microcrystalline wax, preferably from 3 to 15%, more preferably from 5 to 10%.

N. The method according to paragraph L or M wherein the additional microcrystalline wax has a needle penetration at 25° C. of from 40 to 60 dmm.

O. The method according to paragraphs L to N wherein the olfactory composition comprises an olfactory agent selected from the group consisting of levomenthol, camphor, eucalyptus oil, cedar wood oil, turpentine oil, thymol, lavender oil, rosemary oil, peppermint oil, cardamom, ginger, petitgrain, nutmeg oil, cedar leaf oil, and combinations thereof.

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal care composition for application to skin comprising:
   a. from about 35% to about 90% petrolatum, by weight of the personal care composition;
   b. from about 5% to about 10%, by weight of the personal care composition, of an additional microcrystalline wax having a needle penetration at 25° C. of from about 35 to about 75 dmm;
   c. from about 1% to about 6% of a gelling agent mixture, by weight of the personal care composition; and
   d. from about 20% to about 50% of an olfactory composition, by weight of the personal care composition.

2. The personal care composition of claim 1 comprising from about 2.5% to about 5% of the gelling agent mixture, by weight of the personal care composition.

3. The personal care composition of claim 2 wherein the gelling agent mixture comprises a gelling agent comprising dibutyl lauroyl glutamide and dibutyl ethylhexanoyl glutamide.

4. The personal care composition of claim 3 wherein the gelling agent mixture further comprising a solvent selected from the group consisting of pentylene glycol, propylene glycol, and hexylene glycol, 3-methyl-1,3-butanediol, 3-methyl-1,2-butanediol, 1,5-pentanediol, and combinations thereof.

5. The personal care composition of claim 1 wherein the olfactory composition comprises an olfactory agent selected from the group consisting of levomenthol, camphor, eucalyptus oil, cedar wood oil, turpentine oil, thymol, lavender oil, rosemary oil, peppermint oil, cardamom, ginger, petitgrain, nutmeg oil, cedar leaf oil, and combinations thereof.

6. The personal care composition of claim 1 wherein the personal care composition has a vapor release of greater than about 35 mg at 8 hours as measured by the Vapor Release Test Method.

7. The personal care composition of claim 1 wherein the personal care composition has a vapor release of about 35 mg to about 300 mg at 8 hours as measured by the Vapor Release Test Method.

8. A method of suppressing a cough by administering the personal care composition of claim 1.

9. A personal care composition for application to skin comprising:
   a. from about 35% to about 90% petrolatum, by weight of the personal care composition;
   b. from about 5% to about 10%, by weight of the personal care composition, of an additional microcrystalline wax wherein the microcrystalline wax has a needle penetration at 25° C. of from about 35 to about 75 dmm; and
   c. from about 20% to about 50% of an olfactory composition, by weight of the personal care composition.

10. The personal care composition of claim 9 wherein the additional microcrystalline wax has a drop melting point of from about 60° C. to about 77° C.

11. The personal care composition of claim 9 wherein the personal care composition is in a form selected from the group consisting of a viscous liquid, a gel, a paste, and combinations thereof.

12. The personal care composition of claim 9 further comprising from about 1% to about 8% of a gelling agent mixture, by weight of the personal care composition.

13. A personal care composition for application to skin comprising:
   a. from about 35 to about 90% petrolatum, by weight of the personal care composition;
   b. from about 5% to about 10%, by weight of the personal care composition, of an additional microcrystalline wax having a needle penetration at 25° C. of from about 35 to about 75 dmm; and
   c. an olfactory composition;
      wherein the personal care composition has vapor release of greater than about 35 mg at 8 hours as measured by the Vapor Release Test Method.

14. The personal care composition of claim 13 wherein the personal care composition comprises a weight ratio of the additional microcrystalline wax to petrolatum of from about 1:3 to about 1:15.

15. The personal care composition of claim 13 wherein the olfactory composition comprises an olfactory agent selected from the group consisting of levomenthol, camphor, eucalyptus oil, cedar wood oil, turpentine oil, thymol, lavender oil, rosemary oil, peppermint oil, cardamom, ginger, petitgrain, nutmeg oil, cedar leaf oil, and combinations thereof.

16. The personal care composition of claim 13 wherein the personal care composition has vapor release of greater than about 50 mg at 8 hours as measured by the Vapor Release Test Method.

\* \* \* \* \*